United States Patent
Marin et al.

(10) Patent No.: US 11,659,989 B2
(45) Date of Patent: May 30, 2023

(54) APPARATUS AND METHOD FOR MEASURING SUBJECTIVE OCULAR REFRACTION WITH HIGH-RESOLUTION SPHERICAL AND/OR CYLINDRICAL OPTICAL POWER

(71) Applicant: Essilor International, Charenton-le-Pont (FR)

(72) Inventors: Gildas Marin, Charenton-le-Pont (FR); Philippe Pinault, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 1014 days.

(21) Appl. No.: 16/467,337

(22) PCT Filed: Oct. 23, 2017

(86) PCT No.: PCT/FR2017/052915
§ 371 (c)(1),
(2) Date: Jun. 6, 2019

(87) PCT Pub. No.: WO2018/104600
PCT Pub. Date: Jun. 14, 2018

(65) Prior Publication Data
US 2020/0069174 A1 Mar. 5, 2020

(30) Foreign Application Priority Data
Dec. 7, 2016 (FR) ........................................ 1662083

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0058* (2013.01); *A61B 3/0285* (2013.01); *A61B 3/036* (2013.01); *A61B 3/04* (2013.01); *G02B 3/0081* (2013.01)

(58) Field of Classification Search
CPC ....... A61B 3/028; A61B 3/0285; A61B 3/032; A61B 3/036; A61B 3/04; G02B 3/0081
See application file for complete search history.

(56) References Cited

U.S. PATENT DOCUMENTS

| | | | |
|---|---|---|---|
| 3,305,294 A | * | 2/1967 | Luisw ................... G02C 7/081 359/708 |
| 6,048,064 A | | 4/2000 | Hosoi et al. |

(Continued)

FOREIGN PATENT DOCUMENTS

| | | |
|---|---|---|
| CN | 102946790 A | 2/2013 |
| EP | 1250883 B1 | 8/2006 |

(Continued)

OTHER PUBLICATIONS

International Search Report, dated Feb. 5, 2018, from corresponding PCT application No. PCT/FR2017/052915.

*Primary Examiner* — Nicholas R. Pasko
(74) *Attorney, Agent, or Firm* — Nixon & Vanderhye

(57) ABSTRACT

Disclosed is an apparatus for measuring subjective ocular refraction including a display device configured to display a least one optotype and a refractive optical system arranged between an eye of a viewer and the display device, the refractive optical system having an optical power that can be varied according to a determined minimum step. The display device further includes a unit for varying optical power designed to generate a variation in the spherical and/or cylindrical optical power, such that the display device and the refractive optical system form a first image of the optotype with a first total optical power and, respectively, a (Continued)

Figure 1:
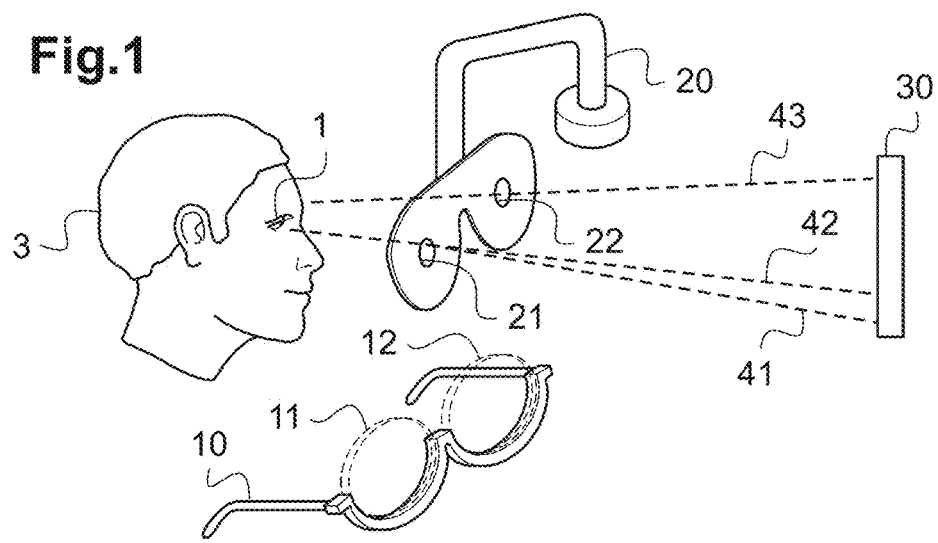

second image of the optotype with a second total optical power, the variation in optical power between the first total optical power and the second total optical power being less than the determined minimum step.

9 Claims, 3 Drawing Sheets

(51) Int. Cl.
    *A61B 3/036*     (2006.01)
    *A61B 3/028*     (2006.01)
    *A61B 3/04*     (2006.01)
    *G02B 3/00*     (2006.01)

(56) References Cited

U.S. PATENT DOCUMENTS

| | | | |
|---|---|---|---|
| 6,749,303 B2 * | 6/2004 | Fukuma | A61B 3/032 351/233 |
| 7,607,778 B2 * | 10/2009 | Oda | H04N 13/324 351/242 |
| 8,292,435 B2 * | 10/2012 | Kanazawa | A61B 3/0285 351/201 |
| 8,596,792 B2 * | 12/2013 | Hirayama | A61B 3/08 351/240 |
| 8,783,871 B2 * | 7/2014 | Pamplona | A61B 3/032 351/239 |
| 8,827,451 B2 * | 9/2014 | Cabeza Guillen | A61B 3/085 351/201 |
| 10,642,355 B1 * | 5/2020 | Gotsch | G06V 10/147 |
| 10,699,373 B1 * | 6/2020 | Gotsch | G06T 5/003 |
| 2004/0100617 A1 | 5/2004 | Abitbol | |
| 2007/0052924 A1 | 3/2007 | Nozawa et al. | |
| 2007/0229762 A1 | 10/2007 | Sakurada et al. | |
| 2012/0002163 A1 * | 1/2012 | Neal | G02B 13/22 351/239 |
| 2013/0201447 A1 * | 8/2013 | Thompson | A61B 3/028 351/201 |
| 2017/0027435 A1 | 2/2017 | Boutinon et al. | |
| 2017/0055825 A1 * | 3/2017 | Tumlinson | A61B 3/0025 |

FOREIGN PATENT DOCUMENTS

| | | |
|---|---|---|
| WO | 02/09579 A1 | 2/2002 |
| WO | 2015/155458 A1 | 10/2015 |

* cited by examiner

Fig.4

| | 4 | 5 | 6 | 7 | 8 | 9 |
|---|---|---|---|---|---|---|
| | E | $*^{-1}$ | 0.25D | E | E | E |
| | | | 0.125D | E | E | E |
| | | | 0D | E | E | E |
| | | | -0.125D | E | E | E |
| | | | -0.25D | E | E | E |

Fig.5

| 4 | 5 | S | C | | | | | | |
|---|---|---|---|---|---|---|---|---|---|
| | | | -0.375D | -0.25D | -0.125D | 0D | 0.125D | 0.25D | 0.375D |
| E | $*^{-1}$ | 0.375D | | | | | | | |
| | | 0.25D | | | | E | | | |
| | | 0.125D | | | E | E | E | | |
| | | 0D | | E | E | E | E | E | |
| | | -0.125D | | | E | E | E | | |
| | | -0.25D | | | | E | | | |
| | | -0.375D | | | | | | | |

Fig.6

Fig.7
| S=0,12D C=0,12D A=90° | S=+0,12D C=0D | S=+0,12D C=0,12D A=0° |
| --- | --- | --- |
| S=0 C=0,12D A=90° | S=0D C=0D | S=0D C=0,12D A=0° |
| S=-0,12D C=0,12D A=90° | S=-0,12D C=0D | S=-0,12D C=0,12D A=0° |
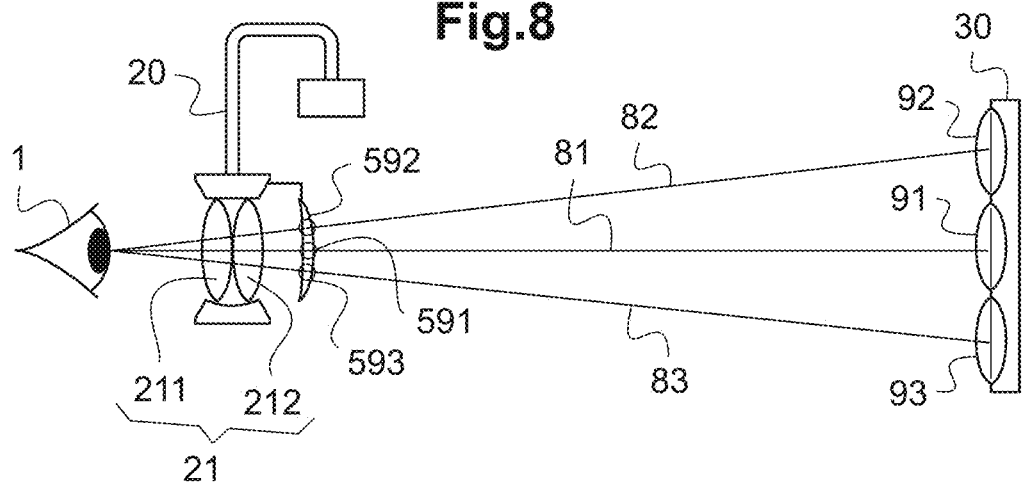
Fig.8
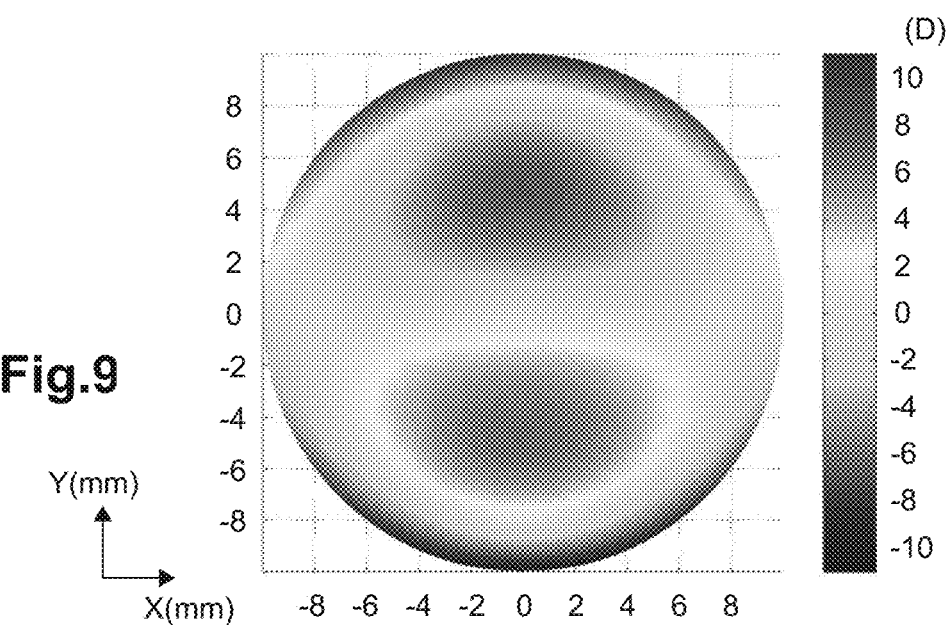
Fig.9

APPARATUS AND METHOD FOR MEASURING SUBJECTIVE OCULAR REFRACTION WITH HIGH-RESOLUTION SPHERICAL AND/OR CYLINDRICAL OPTICAL POWER

TECHNICAL FIELD OF THE INVENTION

Generally, the present invention relates to the field of optometric apparatuses and methods.

It more particularly relates to an apparatus and method for measuring subjective ocular refraction and/or testing a person for astigmatism.

It in particular relates to an apparatus for measuring subjective ocular refraction comprising means for taking a high-precision measurement of cylindrical and/or spherical optical power.

It also relates to a method for converting a conventional apparatus for measuring subjective ocular refraction having a limited resolution in optical power into a high-precision apparatus.

TECHNOLOGICAL BACKGROUND

In the context of the measurement of the subjective ocular refraction of a subject, it has already been proposed to simulate the visual compensation to be provided, for example by means of a trial frame or a refractor such as a phoropter.

A trial frame may successively receive trial lenses providing different spherical and/or cylindrical corrections, so as to determine the correction best suited to the patient.

This solution requires trial lenses to be stored separately in dedicated boxes. It furthermore involves lens changes, resulting in undesired and discontinuous transitions in corrective power. Trial lenses are in general produced with a cylindrical and/or spherical power that may be varied in steps of at least 0.25 diopters (or 0.25 D).

In phoropters, trial lenses are placed on a plurality of disks that are rotated manually or using a motorized mechanism. However, the variation in optical power is also discontinuous in steps of at least 0.25 diopters.

The precision of the subjective ocular refraction measurement is limited, on the one hand by the ability of the subject to detect a difference between two sequentially displayed optotypes, and on the other hand by the minimum step size of the variation in optical power from one trial lens to the next.

In the present document, an optotype may be a letter, a symbol, such as for example a Landolt C, or, more generally, any design or sign having a sufficient contrast and a sufficient level of detailed to be clearly seen by the subject. The optotypes are preferably designed to have a level of resolution of detail close to the minimum perception of details possible with the human eye.

Apparatuses using a continuous variation in refraction to allow subjective ocular refraction to be measured do exist. However, these apparatuses are generally complex and very specific.

Patent document EP 1250883 B1 describes an optometric apparatus comprising a light source, a target subject, an optical system comprising a cylindrical and/or spherical lens, and a diffraction grating forming, for one eye of an observer, various images of the target, which appear dispersed in a plane transverse to an optical axis and which are displayed simultaneously at various virtual differences along the optical axis. Nevertheless, this system is very complex and has the drawbacks of chromatism and of low effectiveness due to the diffraction in the diffraction grating.

Furthermore, digital image-processing methods exist that allow pre-corrected images of optotypes to be generated without a conventional optical system. However, these digital methods are currently not very precise.

SUBJECT OF THE INVENTION

In order to remedy the aforementioned drawbacks of the prior art, the present invention proposes an apparatus for measuring subjective ocular refraction comprising a viewing device comprising a screen configured to display a least one optotype and a refractive optical system placed between an eye of an observer and the viewing device, the refractive optical system having a cylindrical and/or spherical optical power that may be varied in steps of a determined minimum step size.

According to the invention, the viewing device furthermore includes additional means for varying optical power, said means being suitable for generating a variation in cylindrical and/or spherical optical power so that the viewing device and the refractive optical system form a first image of the optotype with a first total optical power and a second image of the optotype with a second total optical power, respectively, the variation in optical power between the first total optical power and the second total optical power being of nonzero value and lower in absolute value than the determined minimum step size.

Thus, the apparatus allows a measurement of subjective ocular refraction to be obtained with steps that are of very small step size, or that are even continuous.

According to one particular and advantageous aspect of the invention, the viewing device includes an electronic screen that comprises a two-dimensional array of pixels and a two-dimensional array of micro-lenses or of micro-apertures that is placed between the electronic screen and the refractive optical system, and the additional means for varying optical power comprise a system for controlling the display on the electronic screen, the control system being configured to activate a first plurality of pixels selected from among the array of pixels in order to generate the first image of the optotype and to activate a second plurality of pixels selected from among the array of pixels in order to generate the second image of the optotype, respectively.

According to another particular and advantageous aspect of the invention, the viewing device includes an electronic screen that comprises a two-dimensional array of pixels and wherein the additional means for varying optical power comprise an image-processing system, the image-processing system being configured to apply a first pre-correction to generate the first image of the optotype and to apply a second pre-correction to generate the second image of the optotype.

According to one particular embodiment, the additional means for varying optical power comprise a complimentary refractive optical component having a spatially variable optical power. In one example, the additional means for varying optical power comprise an optical component consisting of a plurality of lenses the focal lengths of which are slightly different from one another. In another example, the optical component has aberrations of order higher than 2 so as to generate a spatial variation in optical power. In one particular and advantageous example, the complementary refractive optical component comprises an Alvarez lens, a liquid lens, an active Fresnel lens based on liquid crystals or a spatial modulator of light based on liquid crystals.

According to another particular and advantageous aspect, the additional means for varying optical power comprise another complimentary optical system consisting of a first plate and of a second plate, the first plate having a planar first face and a second face having a two-dimensional profile of cubic polynomial form and the second plate having a planar second face and a first face having a two-dimensional profile of cubic polynomial form, the first face of the second plate being of inverse profile to the second face of the first plate, the second face of the first plate being placed facing the first face of the second plate.

Particularly advantageously, the apparatus includes optomechanical means for translating and/or rotating the complementary refractive optical component or the complementary optical system.

According to one preferred embodiment, the variation in optical power comprises a variation in spherical power and/or a variation in cylindrical power and/or a variation in the orientation of the cylindrical-power axis.

In one particular embodiment, the first image of the optotype and the second image of the optotype are generated, simultaneously, respectively, in a first ocular sight direction and in a second ocular sight direction, respectively.

Advantageously, the first image of the optotype and the second image of the optotype are generated sequentially at different times.

According to one particular aspect, the additional means for varying optical power are suitable for generating a continuous variation in optical power in a limited range of variation in optical power of 0.125 diopters, 0.25 diopters or 0.5 diopters.

Advantageously, the additional means for varying optical power are suitable for generating a variation in optical power having a step size smaller than or equal to half the determined minimum step size of the refractive optical system.

Advantageously, the apparatus includes a holder supporting the viewing device and the refractive optical system, the holder being suitable for being mounted on the head of the observer.

According to one particular aspect, the apparatus furthermore includes a system for tracking head movements suitable for determining at least one ocular sight direction of the eye of the observer.

The invention also relates to a method for converting an apparatus for measuring subjective ocular refraction comprising a viewing device comprising a screen and a refractive optical system placed between an eye of an observer and the viewing device, the refractive optical system having a cylindrical and/or spherical optical power that may be varied in steps of a determined minimum step size, into an apparatus for measuring subjective ocular refraction of higher resolution in cylindrical and/or spherical optical power, the converting method comprising the following steps:
providing another viewing device including another screen configured to display a least one optotype and additional means for varying cylindrical and/or spherical optical power that are suitable for generating a variation in optical power so that the viewing device and the refractive optical system form a first image of the optotype with a first total optical power and a second image of the optotype with a second total optical power, respectively, the variation in optical power between the first total optical power and the second total optical power being of nonzero value and lower in absolute value than the determined minimum step size.

The invention also relates to a method for measuring subjective ocular refraction comprising the following steps:
placing a refractive optical system between at least one eye of an observer and a viewing device, the refractive optical system having an optical power that may be varied in steps of a determined minimum step size, and the viewing device furthermore including additional means for varying cylindrical and/or spherical optical power that are suitable for generating an additional variation in optical power of nonzero value and lower in absolute value than the determined minimum step size,
displaying at least one optotype on a screen of the viewing device so that the viewing device and the refractive optical system form a first image of the optotype,
making the optical power of the refractive optical system vary by the determined minimum step size in order to determine a correction suitable for the eye of the observer;
making the optical power of the additional means for varying optical power vary so that the viewing device and the refractive optical system form a second image of the optotype, in order to determine a correction of higher resolution suitable for the eye of the observer.

DETAILED DESCRIPTION OF AN EXEMPLARY EMBODIMENT

The description which follows with reference to the appended drawings, which are given by way of nonlimiting examples, will make it easy to understand what the invention consists of and how it may be achieved.

Figure 2:
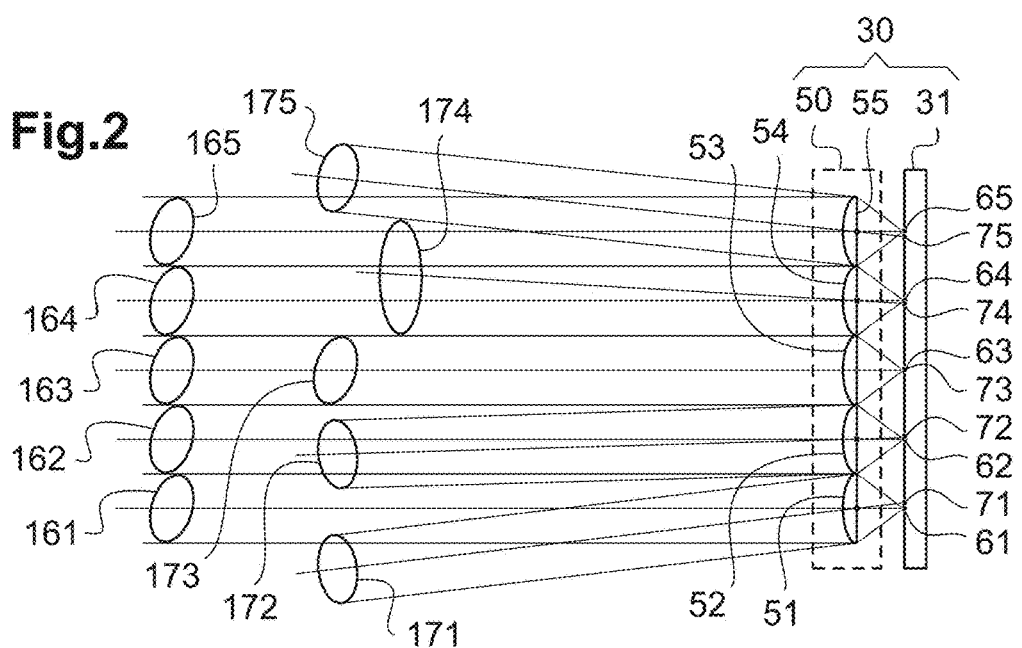
Figure 3:
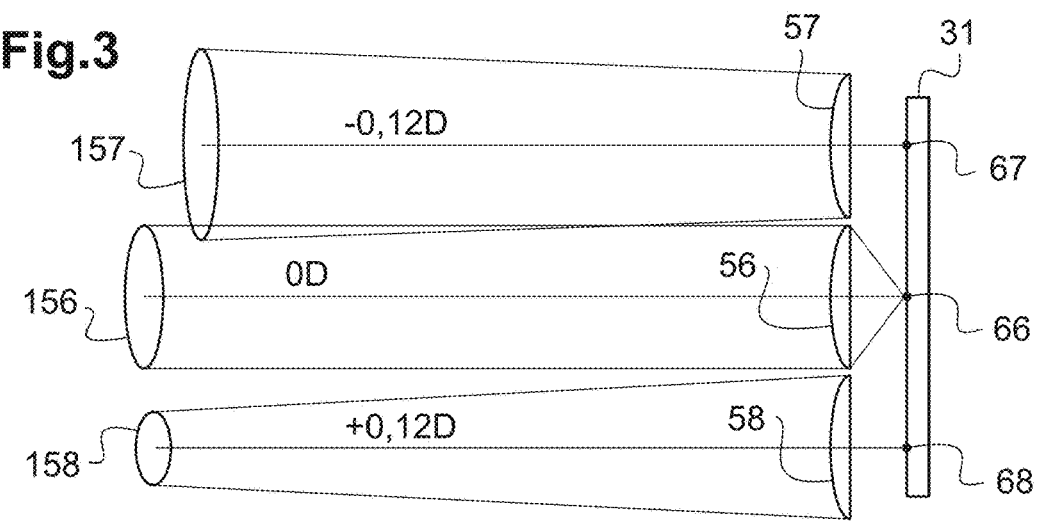

In the appended drawings:

FIG. 1 schematically shows an apparatus for measuring subjective ocular refraction and/or testing a person for astigmatism;

FIG. 2 schematically shows a cross-sectional view of a system for displaying optotypes for an apparatus for measuring subjective ocular refraction according to a first embodiment;

FIG. 3 schematically shows a cross-sectional view of another system for displaying optotypes for an apparatus for measuring subjective ocular refraction according to a variant of the first embodiment;

FIGS. 4 to 7 show various examples of display of panels of optotypes;

FIG. 8 schematically shows an apparatus for measuring subjective ocular refraction according to a second embodiment;

FIG. 9 schematically shows a map of a lens of spatially variable optical power.

DEVICE

FIG. 1 shows an apparatus for measuring subjective ocular refraction and/or testing a person for astigmatism.

The apparatus of FIG. 1 includes a trial frame 10 or a refractor 20 such as for example a phoropter. The apparatus also includes a system 30 for displaying optotypes.

For example, the trial frame 10 is arranged to receive a first trial lens 11 and/or a second trial lens 12. When the subject 3 is wearing the trial frame 10, the first trial lens 11 is placed in front of the right eye 1 of the subject 3 and, respectively, the second trial lens 12 is placed in front of the left eye of the subject 3. The trial lens in general includes a lens. Each lens has an optical power of cylindrical and/or spherical type. The optician selects the optical power of the trial lens 11, 12 from a set of trial lenses each having a predetermined optical power, varying from one lens to the next in steps of at least 0.25 diopters. The cylindrical and/or spherical power of the trial lens is thus variable in steps of at least 0.25 diopters. In the case of a cylindrical trial lens, various orientations of the axis of the cylinder of the trial lens may be tested in order to determine the astigmatism axis of the tested eye, for example according to predetermined orientations equal to 0 degrees, +/−45 degrees, and +/−90 degrees.

Conventionally, a trial lens able to be decomposed mathematically into a spherical lens and two cylindrical lenses, called Jackson cross cylinders, is used to determine the correction in terms of sphere, cylinder and axis. The following denotations will be used below:

Sphor, the spherical optical power of the spherical lens;
J0phor, the optical power of the cylindrical lens at 0 degrees; and
J45phor, the optical power of the cylindrical lens at 45 degrees.

Equivalently, the refractor 20 is configured to place a trial lens 21 in front of the right eye 1 of the substrate 3 and/or another trial lens 22 in front of the left eye of the subject 3. Various trial lenses the optical power of which varies in steps of at least 0.25 diopters are integrated into the refractor. The refractor includes a motorized or manually actuated mechanism for changing the optical power of the trial lens 21 and 22, respectively, placed in front of the right eye 1 and left eye of the subject 3, respectively. The variation in optical power of the trial lens 21, 22 is also discontinuous in steps of at least 0.25 diopters.

The system 30 for displaying optotypes is configured to display at least one first optotype and one second optotype. In the embodiments described in detail below, the system 30 for displaying optotypes may include a passive screen, for example a printed medium, or an active screen such as, for example, an optoelectronic screen. According to certain embodiments, the first optotype and the second optotype are displayed simultaneously and are visible in angularly separate ocular sight directions. According to other embodiments, the first optotype and the second optotype are displayed sequentially, so as to display at one time only the first optotype and at another time only the second optotype.

During the measurement of subjective ocular refraction, the subject 3 views, with his eye 1, through the trial lens 21, the first optotype displayed on the system 30 for displaying optotypes, for example in one ocular sight direction 41. Without moving his head, the subject 3 may also view, with his eye 1, through the trial lens 21, the second optotype displayed on the system 30 for displaying optotypes, for example in a second ocular sight direction 42.

According to the present disclosure, the system 30 for displaying optotypes includes additional means for varying optical power that are suitable for generating an additional variation in cylindrical and/or spherical optical power that is lower in absolute value than the minimum step size of variation in optical power of the trial lens. More precisely, this additional variation in cylindrical and/or spherical optical power may be continuous or incremental in steps of 0.125 diopters. Thus, a preciser measurement of subjective refraction is obtained than with only the phoropter or the trial frame.

The structure and operation of an apparatus for measuring subjective ocular refraction according to a first embodiment, illustrated in FIG. 2, will now be described in detail.

In this first embodiment, a trial frame 10 or a conventional refractor 20 and a system 30 for displaying optotypes of the light-field display (LSD) type are used. More precisely, the system 30 for displaying optotypes includes an optoelectronic viewing screen 31 having a one-dimensional or, preferably, two-dimensional matrix array of pixels. In the example of FIG. 2, the system 30 for displaying optotypes includes a microlens array 50. The microlens array 50 includes a plurality of lenses 51, 52, 53, 54, 55 arranged in a regular tiling in the same plane, parallel to the plane of the viewing screen 31. Each microlens 51, 52, 53, 54, 55 has a focal point located on a pixel 61, 62, 63, 64, 65 of the screen 31, respectively.

The pixels 61, 62, 63, 64 and/or 65 are selectively activated in order to display a point of a first optotype. Each microlens 51, 52, 53, 54, 55 forms a collimated beam 161, 162, 163, 164, 165 from the point source formed by each pixel 61, 62, 63, 64, 65, respectively. The collimated beams 161, 162, 163, 164, 165 are here all parallel to one another. Thus, an image of the point of the first optotype is formed by selectively activating a first set of pixels 61, 62, 63, 64 and/or 65. With respect to the eye 1 of the observer viewing the beams 161, 162, 163, 164 and/or 165 through the trial lens 21, the image of the point of the first optotype is located at a first apparent distance, here at infinity, on a first ocular sight axis 41.

Simultaneously or sequentially, other pixels 71, 72, 73, 74 and/or 75 are selectively activated in order to display a point of a second optotype. These other pixels 71, 72, 73, 74 and/or 75 are in general offset laterally with respect to the pixels 61, 62, 63, 64, 65 located on the focal points of the microlens array. Thus, each microlens 51, 52, 53, 54, 55 forms another beam 171, 172, 173, 174, 175 from the point source formed by each pixel 71, 72, 73, 74, 75, respectively. The inclination of the beam 171 depends on the lateral offset between the pixel 71 and the pixel 61 located at the focal point of the microlens 51. Analogously, the inclination of each beam 172, 173, 174, 175 depends on the lateral offset between each pixel 72, 73, 74, 75 and the pixel 62, 63, 64, 65 located at the focal point of the microlens 52, 53, 54, 55, respectively. Together all of the beams 171, 172, 173, 174, 175 thus generate an image of the point of the second optotype. Thus, an image of the point of the second optotype is formed by selectively activating a second set of pixels 71, 72, 73, 74 and/or 75. With respect to the eye 1 of the observer viewing the beams 171, 172, 173, 174 and/or 175 through the trial lens 21, the image of the point of the second optotype is located at another apparent distance to the image of the first optotype. To facilitate representation, the pixels 61, 62, 63, 64, 65 and the pixels 71,72, 73, 74,75 have been shown in one zone of the screen 31. In practice, to obtain a spatial separation, these pixels 61, 62, 63, 64, 65 on the one hand and 71, 72, 73, 74, 75 on the other hand are displayed in separate zones of the screen 31.

Analogously, it is possible to selectively activate other pixels in order to display other points of the first and second optotype simultaneously, in order to display all of the points of the first and second optotypes.

Nevertheless, the simultaneously displayed optotypes are configured so that their respective images are spatially separate as seen by the eye 1 of the observer through the trial lens 21.

Thus, the observer may view, at the same time, a plurality of optotypes and by comparison of the images of the first optotype, of the second optotype and of the third optotype easily determine the image that appears to be the clearest.

In other words, by setting the position of the active pixels with respect to the centers of the lenses, it is thus possible to simulate various wavefronts, which may be spherical or cylindrical. In the latter case, the spacing between the pixels is not the same in a horizontal or vertical direction.

Generally, when the spacing between the active pixels 61, 62 is equal to the spacing between micro-lenses 51, 52, then the light beams 161, 162 output from these pixels 61, 62 are parallel to each other and seen to be a point at infinity. When the spacing between the active pixel 73, 74 is larger than the spacing between micro-lenses 53, 54, the beams 173, 174 are seem to be convergent beans, thus simulating a positive power. When the spacing between the active pixel 74, 75 is smaller than the spacing between micro-lenses 54, 55, the beams 174, 175 are seem to be divergent beans, thus simulating a negative power.

The difference in apparent distance between the image of the first optotype and the image of the second optotype with respect to the eye 1 of the observer is equivalent to a difference in optical power. The system 30 for displaying optotypes is configured so that this difference in optical power is smaller than the minimum difference, i.e. step size, in power between two available trial lenses. For example, the minimum step size being equal to 0.25 diopters of power, the system for displaying optotypes is configured to generate a difference in optical power between the image of the first optotype and the image of the second optotype equivalent to 0.20 diopters, or 0.125 diopters all 0.10 diopters or 0.05 diopters.

The additional optical powers generated by the viewing system 30 are denoted Sdisplay, J0display and J45display. More precisely, the additional optical powers generated by the viewing device corresponding to the first optotype are denoted Sdisplay1, J0display1 and J45display1. Likewise, the additional optical powers generated by the viewing device corresponding to the second optotype are denoted Sdisplay2, J0display2 and J45display2. The difference between Sdisplay1 and Sdisplay2 is smaller than the minimum step of variation in spherical power of the trial lens. Likewise, the difference between J0display1 and J0display2 (between J45display1 and J45display2, respectively) is smaller than the minimum step of variation in cylindrical power of the Jackson cross cylinders of the trial lens.

The observer 3 observes the image of the first optotype on the viewing system 30 through the trial lens, and therefore through an optical system having a total optical power equal to the sum of the optical power of the trial lens and of the additional optical power of the viewing system 30. The observer 3 thus perceives the first optotype with total optical powers S-1, J0-1, J45-1 equal to 5-1=Sphor+Sdisplay1, J0-1=J0phor+J0display1 and J45-1=J45phor+J45display1, respectively. Analogously, the observer 3 perceives the second optotype with total optical powers S-2, J0-2, J45-2 equal to S-2=Sphor+Sdisplay2, J0-2=J0phor+J0display2 and J45-2=J45phor+J45display2, respectively. The variation in optical power between (S-1, J0-1, J45-1) and (S-2, J0-2, J45-2) is smaller than the minimum step of variation of the trial lens.

By choosing a very high-resolution screen 31 of matrix array pixels, it is thus possible to generate an optical power difference that varies in extremely small steps, almost continuously. Thus, it is possible to obtain a preciser refraction measurement then with available trial lenses.

The amplitude of the additional variation in optical power thus accessible is limited to a small range, for example from −0.5 to +0.5 diopters but with a precision (or a step size) that is improved with respect to that of the trial lenses 21, 22. Given an adaptation of the display system 30, a professional may use a phoropter or a conventional trial frame to perform a preciser measurement of refraction, without needing to use a specific and complex item of equipment.

Thus, it is enough to replace the conventional screen of a conventional phoropter with a new viewing system comprising additional means for varying optical power in steps of small size to considerably improve the refraction-measurement precision.

FIG. 3 schematically shows a cross-sectional view of another system for displaying optotypes for an apparatus for measuring subjective ocular refraction according to a variant of the first embodiment;

The display system of FIG. 3 includes a screen 31 and an additional optical system placed between the screen 31 and the trial lens 21. The screen 31 is preferably of optoelectronic type. In the example of FIG. 3, the additional optical system includes a first lens 56, a second lens 57 a third lens 58. The first lens 56 is placed in front of a first zone 66 of the screen 31. Analogously, the second lens 57 is placed in front of a second zone 67 of the screen 31. The third lens 58 is placed in front of a third zone 68 of the screen 31. The first lens 56, the second lens 57 and the third lens 58 each have a different cylindrical and/or spherical optical power.

The first lens 56 is for example arranged such that its focal point is located on the screen 31. The first lens 56 forms a collimated beam 156 from the source formed by a first optotype located in the first zone 66 of the screen. The first lens 56 thus generates the equivalent of a zero optical power (0 D).

The second lens 57 is for example arranged such that its focal point is located further than the screen with respect to this second lens. The second lens 57 forms a divergent second beam 157 from the source formed by a second optotype located in the first zone 67 of the screen. The second lens 57 thus generates the equivalent of a complementary optical power of −0.12 diopters.

The third lens 58 is for example arranged such that its focal point is located between the screen 31 and the third lens 58. The third lens 58 forms a convergent third beam 158 from the source formed by a third optotype located in the third zone 68 of the screen. The third lens 58 thus generates the equivalent of a complementary optical power of +0.12 diopters.

In FIG. 3, the first lens 56 forms the image of a first optotype displayed in the first zone 66 of the screen and simultaneously, the second lens 57 forms the image of a second optotype displayed in the second zone 67 of the screen. Analogously, the third lens 58 forms the image of a third optotype displayed in the third zone 68 of the screen 31. The eye 1 of the observer 3 thus simultaneously views through a trial lens 21 an image of the first optotype, an image of the second optotype and an image of the third optotype. These images are spatially separate while being affected by a complementary power difference that adds to the optical power of the trial lens 21.

In another embodiment, a display system taking the form of a panel of optotypes, in which each optotype image is preprocessed so as to simulate a complementary cylindrical and/or spherical power, is used. The image preprocessing is for example based on a deconvolution by an optical transfer function of a complementary optical power. In another example, the image preprocessing is based on a calculation of the modification to ray path induced by a complementary optical power.

The panel may be one-dimensional or two-dimensional with an unmodified central optotype and peripheral optotypes modified to correspond to a stepped change in the correction of given size, for example of one ¼ of a diopter or ⅛ of a diopter size. Advantageously, the correction is symmetric and of opposite sign on either side of the central optotype. The panel may include an uneven number of rows and/or columns, for example comprising 3×3, 5×5 or 7×7 optotypes.

By way of example, the panel of FIG. 4 shows in column 4 a source optotype without image processing. Column 5 schematically shows the employed image-processing function, for example a function for deconvoluting an optical transfer function of a complimentary optical power or a computation of the modification to ray path induced by a complementary optical power. Column 6 shows the equivalent differences in optical power applied to form a first optotype (at 0 D), a second optotype (+0.125 D), a third optotype (−0.125 D), a fourth optotype (+0.25 D) and a fifth optotype (−0.25 D), respectively. An optotype scale simulating a complementary correction ranging from −0.25 D to +0.25 D in steps of 0.125 D is thus formed. Column 7 shows how the optotype scale appears to an observer having no need for any correction. The first optotype (0 D) at the center of column 7 appears clearest, haziness increasing symmetrically for the other optotypes as a function of the increasing difference in power. Column 8 shows how the optotype scale appears to an observer having a need for a correction of −0.125 D. The third optotype (−0.125 D) of column 8 now appears clearest, haziness increasing symmetrically about this third optotype (−0.125 D). Column 9 shows how the optotype scale appears to an observer having a need for a correction of +0.125 D. The second optotype (+0.125 D) of column 9 here appears clearest, haziness increasing symmetrically about this second optotype (+0.125 D). It is assumed here that the observer does not accommodate. In the contrary case, it is possible for not only the image corresponding to his refraction to appear clear, but also as many images corresponding to a negative power as he has ability to accommodate.

The panel of FIG. 5 uses two dimensions to simultaneously test the required modification with respect to 2 correction parameters among sphere, cylinder and axis (or M, J0 and J45). In this table, the rows correspond to a complementary spherical correction ranging from −0.375 D to +0.375 D in steps of 0.125 D. In this table, columns correspond to a complementary cylindrical correction ranging from −0.375 D to +0.375 D in steps of 0.125 D.

The subject 3 simultaneously views all the optotypes of the table, this allowing him to easily compare the clearness of the various optotype images with steps of difference in optical power of very small size. In this example, the observer sees clearly the optotype corresponding to a complementary optical power S=0 and C=0. In this case, the trial lens exactly corrects the refraction of the observer. In the case where the observer perceives another optotype among the panel to be clearer, he is able to read the required complementary optical power directly from the vertical scale of spherical correction and from the horizontal scale of cylindrical correction.

FIG. 6 illustrates, for example, a screen 31 divided into nine zones, which allows both spherical power, cylindrical power and the axis of the cylinder to be varied in steps of small size. Here, the observer perceives the zone 67 more clearly than all the other zones, for example 68 and 69 of the panel.

FIG. 7 shows the sphere, cylinder and axis values corresponding to each zone of FIG. 6. The operator may thus determine the additional correction in terms of sphere, cylinder an axis to be added to the correction indicated by the trial lens.

The screen simultaneously displays a plurality of optotypes (here a series of letters: AEZT) in each zone corresponding to one different cylindrical and/or spherical optical power.

Preferably, the same forms of optotypes are displayed in the various zones, in order to facilitate the visual comparison by the subject.

The subject indicates the direction in which the change is better, i.e. the direction in which the optotypes appear clearest. The correction of the phoropter is modified accordingly, so as to re-center the clearest optotype in the panel and so on iteratively until a correction is obtained with which the optotype is seen with a haziness that increases perfectly symmetrically on either side of the central optotype.

In the case of a screen combined with a matrix array of lenses (as illustrated in FIG. 3), the zones of FIG. 4 ideally correspond to the various zones 66, 67, 68 defined by the geometry of the lenses 56, 57, 58.

FIG. 8 shows an apparatus for measuring subjective ocular refraction according to a third embodiment. In this third embodiment, a conventional display system employed in combination with the phoropter or trial frame is used. The phoropter 20 for example includes a trial optical system for example including a spherical trial lens 211 and a cylindrical trial lens 212 defining a first correction, which may be relatively coarse depending on the step size of variation in power of the trial lenses, which in general is ¼ D.

The apparatus furthermore includes a supplementary lens 59 having a spatial variation in power over its surface. This supplementary lens 59 is for example added to a trial frame or position between the phoropter 20 and the screen, as illustrated in FIG. 8. The lens 59 is aspherical and generates geometric optical aberrations, for example of coma type.

FIG. 9 schematically illustrates a graphical representation of the spatial variation in optical power of a lens that has zero power at its center, that generates 0.1 µm of coma (Zernike coefficient Z of 3.3) and that is of 20 mm diameter. This lens allows a spatial variation in power of about 0.1 D/mm to be generated along the Y-axis of the coma (vertical axis in FIG. 9) giving a maximum at the edges of +/−1 D and a similar variation in astigmatism along the X-axis. Rotation of the lens allows the axis of variation of the power to be modified.

To make the power vary, the apparatus advantageously includes an optomechanical device for moving this supplementary lens 59 so as to place one particular zone of the supplementary lens on the visual axis of the subject. The movement of the lens 59 (in direction and in amplitude) allows the variation in added optical power to be set.

In the example of implementation illustrated in FIG. 8, the entire area of the supplementary lens 59 is used. In this case, the display system preferably presents to the subject a screen 30 including a plurality of zones 91, 92, 93 for displaying optotypes, these zones 91, 92, 93 being spatially separate. Each zone 91, 92, 93 of the screen is associated with one zone 591, 592, 593 of the supplementary lens 59, respectively. The sight axis of the eye 1 of the subject scans the various zones of the lens and therefore the various zones of the screen in order to test the various refraction values.

These zones may be displayed sequentially, or preferably simultaneously.

The subject, by decentring the lens in front of his eye, selects the preferred vision zone. Knowledge of the correction of the trial lenses 211, 212, of the exact position of the eye and of the variation induced by the lens 59 allows a new correction to be deduced.

This apparatus allows cylindrical and spherical power to be continuously varied, this thus allowing the resolution of the employed apparatus for measuring subjective ocular refraction, independently of whether it is a phoropter or a trial frame, to be increased.

This apparatus allows optotypes corresponding to a difference in cylindrical and/or spherical optical power that is relatively small and in any case smaller than the step size of variation in power of trial lenses to be simultaneously displayed.

In one variant, another complimentary optical system is placed in front of the viewing screen. This other optical system for example consists of a liquid lens. In another example, the complementary optical system consists of an active Fresnel lens based on liquid crystals or of a liquid-crystal device forming a tiling of one or more active Fresnel lenses. An active Fresnel lens may be driven electrically in order to generate or not a complementary optical power.

In another variant, another complimentary optical system consisting of two plates is employed, the first plate having a planar first face and a second face having a two-dimensional profile of cubic polynomial form and the second plate having a planar second face and a first face having a two-dimensional profile of cubic polynomial form, the first face of the second plate being of inverse profile to the second face of the first plate, the second face of the first plate being placed facing the first face of the second plate. By translating the second plate with respect to the first plate, a spatial variation in optical power is thus introduced for example at orders higher than the second order.

According to another embodiment (not shown in the figures), the viewing system is integrated into a holder intended to be mounted directly on the head of the subject 3. For example, the apparatus for measuring refraction takes the form of a virtual reality headset or augmented reality glasses. The holder is able to receive the trial lenses of variable optical power. In addition, the holder includes a viewing system according to one of the embodiments described above. Advantageously, the holder allows an additional optical system to be integrated, which is placed between the trial lens and the viewing screen. This embodiment has the advantage of being very compact. This embodiment allows complimentary optical systems based on liquid lenses, Alvarez lenses, active Fresnel lenses and/or plates of polynomial profile of small size to be used. The movement of the head allows a scan over 360° of various combinations of additional corrections. Thus, the complementary cylinder/sphere pairs are navigated by moving the head along 2 axes. The choice is thus made intuitively and naturally.

Particularly advantageously, the apparatus furthermore includes a system for tracking head movements (or head tracker) suitable for determining the posture of the subject and/or for determining a direction of ocular sight of the eye of the observer.

Thus, the position of the gaze fixating on the clearest image is determined, this allowing the complementary correction in sphere/cylinder to be determined by selecting the corresponding image.

Method

The measurement of subjective ocular refraction may be carried out in various ways using any one of the apparatuses described above.

In one example of a measuring method, a conventional first refraction-measuring step is firstly carried out without using the display system and/or the additional optical component to make the optical power vary in steps of smaller size.

Next, in a second step, the measurement is refined with a smaller step size. A variation in power of small amplitude and of small step size about the first refraction measurement found in the first step is introduced. For example, in FIG. 6, if the subject preferred the clearness of the test at the top right of the panel, his conventionally measured refraction and the complimentary refraction are corrected. In this example, the final spherical correction is equal to the spherical correction determined in step 1 to which a complementary spherical correction of +0.12 D is added.

In another example, various optotypes corresponding to various variations in complementary spherico-cylindrical refraction power are simultaneously displayed by means of the complementary optical system and/or of the display system.

Preferably in this case, the central value of the displayed optotype corresponds to a zero cylindrical and spherical complementary correction (S=0 D, C=0 D). Depending on the response of the wearer as to the preferred clearness in the display panel, the power of the trial lens is dynamically modified. Thus, in the example illustrated in FIG. 6, the cylindrical and spherical refraction power is gradually increased. The refraction measurement is stopped when the best clearness is obtained for the optotype at the center of the panel.

Thus, it is possible to rapidly determine in which sense to modify the refraction to achieve the optimal value.

Advantageously, a human-machine interface (HMI) allowing the refraction to be more easily determined with a high precision and resolution is proposed in the present disclosure.

The aim is to provide a method for measuring subjective refraction that is easily usable by a person unfamiliar with the field of refraction and without assistance from a qualified operator.

The general solution is to use the simultaneous display of images having various sphere/cylinder/axis powers in order to assist the user in finding, as intuitively as possible, the refraction that precisely meets his needs.

Embodiment No. 1

The desire is to display a set of solutions (Rx) defined on 3 axes (Sph, Cyl, Axe), while allowing the user to navigate simply and intuitively in this space in order to find the ideal trio. An implementation on a screen limits the space to 2 dimensions.

Various implementations are possible.

Step 1: Determining whether the patient is an astigmat via a simple test using a test chart such as an astigmatic dial.

If certain lines appear grey and others blacker (or certain lines hazy and others clearer) then the patient is an astigmat. The axis of the astigmatism will be noted. This test will be carried out sequentially on each of the two eyes, one eye then the other being covered.

Step 2.1: If the patient is not an astigmat, the only value to be measured is the sphere (no cylinder). In one embodiment, the screen displays deconvoluted images corresponding to various sphere powers. If an image is appears clear to the patient, it means that the sphere corresponding to his Rx is that used for the deconvolution of the image. To achieve a simplified user experience, the patient navigates with the left/right arrows of a keyboard if the test is carried out on a computer or by making the images scroll if the periphery has a touchscreen (smart phone or tablet computer for example). This test must be carried out independently on each eye, one eye then the other being covered.

Step 2.2: If the patient is an astigmat, it is assumed that the one or more axes of his astigmatism are known; it is then a question of determining a value for sphere power and a value for cylinder power. The various values of S and C may be presented in two dimensions. For example, deconvoluted images corresponding to various pairs of sphere and cylinder are displayed. If an image appears clear to the patient, it means that this sphere/cylinder pair corresponds to his refraction measurement. For a simplified user experience, the patient navigates sphere with the left/right arrows of a keyboard and cylinder with the up/down arrows if the test is carried out on a computer or by making the images scroll if the periphery has a touchscreen (smart phone or tablet computer for example). This test must be carried out independently on each eye, one eye then the other being covered.

Particularly advantageously, if the apparatus furthermore includes a system for tracking head movements (or head tracker) suitable for determining the posture of the subject and/or for determining an ocular sight direction of the eye of the observer, the position of the gaze fixating the clearest image is determined, this allowing the complementary correction in sphere/cylinder to be determined by selecting the corresponding image.

The invention claimed is:

1. An apparatus configured to measure subjective ocular refraction, the apparatus comprising:
    a viewing device comprising
        a light-field display including an electronic screen comprising a two-dimensional array of pixels and a two-dimensional array of micro-lenses or micro-apertures, the electronic screen configured to display at least one optotype, and
        a control system configured to control the display on the electronic screen; and
    a refractive optical system configured to be disposed in front of an eye of an observer and between the eye and the viewing device, the refractive optical system having a cylindrical and/or spherical optical power that is able to be varied in steps of a determined minimum step size of at least 0.25 diopters,
    wherein the light-field display is configured to generate a variation in the cylindrical and/or spherical optical power in a limited range of variation in optical power of ±0.125 diopters, the variation in optical power of the light-field display having a step size smaller than or equal to half the determined minimum step size of the refractive optical system so that the viewing device and the refractive optical system form a first image of the optotype with a first total optical power and a second image of the optotype with a second total optical power, respectively, the variation in optical power between the first total optical power and the second total optical power being of nonzero value and lower in absolute value than half the determined minimum step size,
    wherein the two-dimensional array of micro-lenses or micro-apertures is disposed between the electronic screen and the refractive optical system,
    wherein the control system is configured to activate a first plurality of pixels selected from the two-dimensional array of pixels in order to generate the first image of the optotype and activate a second plurality of pixels selected from the two-dimensional array of pixels in order to generate the second image of the optotype, respectively, and
    wherein the viewing device and the refractive optical system are configured to simultaneously generate the first image of the optotype in a first direction of ocular sight and the second image of the optotype in a second direction of ocular sight, respectively, so that the observer is able to compare clearness of the first image of the optotype and clearness of the second image of the optotype.

2. The apparatus as claimed in claim 1, further comprising another complimentary optical system consisting of a first plate and a second plate, the first plate having a planar first face and a second face having a two-dimensional profile of cubic polynomial form, the second plate having a planar second face and a first face having a two-dimensional profile of cubic polynomial form, the first face of the second plate being of inverse profile to the second face of the first plate, the second face of the first plate being disposed facing the first face of the second plate.

3. The apparatus as claimed in claim 1, wherein the variation in optical power comprises one or more of: (i) a variation in spherical power, (ii) a variation in cylindrical power, and (iii) a variation in the orientation of the cylindrical-power axis.

4. The apparatus as claimed in claim 1, wherein the control system is configured to generate a continuous variation in optical power in a limited range of variation in optical power of one of 0.125 diopters, 0.25 diopters, and 0.5 diopters.

5. The apparatus as claimed in claim 1, further comprising a head tracker configured to determine at least one ocular sight direction of the eye of the observer.

6. The apparatus as claimed in claim 1, further comprising an image-processing system configured to apply a first pre-correction to generate the first image of the optotype and to apply a second pre-correction to generate the second image of the optotype.

7. The apparatus as claimed in claim 6, further comprising a complimentary refractive optical component having a spatially variable optical power.

8. The apparatus as claimed in claim 1, further comprising a complimentary refractive optical component having a spatially variable optical power.

9. The apparatus as claimed in claim 8, wherein the complementary refractive optical component comprises one of an Alvarez lens, a liquid lens, an active Fresnel lens based on liquid crystals, and a spatial modulator of light based on liquid crystals.

* * * * *